United States Patent [19]

Birkmayer

[11] Patent Number: 5,712,259
[45] Date of Patent: Jan. 27, 1998

[54] NADH AND NADPH PHARMACEUTICALS FOR TREATING CHRONIC FATIGUE SYNDROME

[75] Inventor: Joerg G. D. Birkmayer, Vienna, Australia

[73] Assignee: Birkmayer Pharmaceuticals, New York, N.Y.

[21] Appl. No.: 636,202

[22] Filed: Apr. 22, 1996

[51] Int. Cl.⁶ ........................................... A61K 31/70
[52] U.S. Cl. ...................... 514/52; 514/45; 514/46; 514/47; 536/26.13; 536/26.23; 536/26.24
[58] Field of Search ........................ 514/45, 46, 47, 514/53, 52; 536/26.13, 26.23, 26.24

[56] References Cited

U.S. PATENT DOCUMENTS

| | | | |
|---|---|---|---|
| 4,970,200 | 11/1990 | Birkmayer et al. | 514/52 |
| 5,019,561 | 5/1991 | Birkmayer | 514/52 |
| 5,189,022 | 2/1993 | Bridge et al. | 514/16 |
| 5,267,570 | 12/1993 | Preston | 128/731 |
| 5,312,817 | 5/1994 | Snorrason | 514/923 |
| 5,332,727 | 7/1994 | Birkmayer | 514/52 |
| 5,424,300 | 6/1995 | Uchida | 514/54 |
| 5,444,053 | 8/1995 | Birkmayer | 514/52 |
| 5,545,670 | 8/1996 | Bissbort et al. | 514/52 |

FOREIGN PATENT DOCUMENTS

| | | |
|---|---|---|
| 2057456 | 7/1992 | Canada . |
| 2135203 | 9/1993 | Canada . |
| 0 256 472 | 2/1988 | European Pat. Off. . |
| 0 496 479 B1 | 7/1992 | European Pat. Off. . |
| 0 615 747 A1 | 9/1994 | European Pat. Off. . |
| 63-301810 | 12/1988 | Japan . |
| 92/0275 | 12/1992 | South Africa . |

*Primary Examiner*—James O. Wilson
*Attorney, Agent, or Firm*—Kenyon & Kenyon

[57] ABSTRACT

A method for treating Chronic Fatigue Syndrome or alleviating symptoms thereof wherein the reduced form of nicotinamide adenine dinucleotide (NADH) or the reduced form of nicotinamide adenine dinucleotide phosphate (NADPH) or physiologically compatible salts or derivatives of NADH and/or NADPH are administered to a person suffering from the syndrome or its symptoms. Patients so treated exhibit greatly improved physical strength and performance over time, and their symptoms including fatigue, muscle pain and weakness, and headaches are greatly alleviated.

10 Claims, No Drawings

NADH AND NADPH PHARMACEUTICALS FOR TREATING CHRONIC FATIGUE SYNDROME

BACKGROUND OF THE INVENTION

1. Field of the invention

The invention relates to a pharmaceutical and a method for treating Chronic Fatigue Syndrome and alleviating the symptoms thereof. More particularly, the invention relates to the use of reduced forms of nicotinamide-adenine-dinucleotide (NADH) or nicotinamide-adenine-dinucleotide phosphate (NADPH), or physiologically acceptable salts or derivatives thereof, in the treatment of Chronic Fatigue Syndrome.

2. Description of Related Art

Chronic Fatigue Syndrome (CFS) is an illness characterized by debilitating fatigue and a number of associated symptoms. In September of 1989, the U.S. Center for Disease Control initiated a physician-based Chronic Fatigue Syndrome Surveillance System in four cities to determine the prevalence, incidence, cause and impact of the illness. To date no definitive information has been harvested which applies to CFS as an easily diagnosable malady.

One of the original and remaining diagnostic criteria for CFS is severe, debilitating and unexplainable fatigue, which the patient has experienced and which has lasted for at least the preceding six months.

A more recent revised definition of CFS includes criteria this and is based on a multi-dimensional assessment of fatigue and a functional status of the patient. The modiefied health assessment questionnaire, MOS-36, provides a mechanism for a physician to collect relevant patient status information.

At the present time, there is no known substance which alleviates the severe and debilitating fatigue continously experienced by persons suffering from CFS. Thus, a need exists for a medicine which is effective in treating Chronic Fatigue Syndrome, or at least abating the symptoms thereof.

Nicotinamide-adenine-dinucleotide in its reduced form ("NADH") and nicotinamide-adenine-phosphate-dinucleotide in its reduced form ("NADPH") are physiological substances which occur in all living cells including human cells. These substances are cofactors for a variety of enzymes, the majority of which catalyze oxidation-reduction reactions. Prior to recent discoveries as to certain therapeutic properties of these compounds, their principal utility has been as diagnostic tools in clinical biochemistry and as essential components in reaction kits, for example, in measuring lactatdehydrogenase (LDH).

The most important function of NADH is its driving force for cell respiration. When using oxygen, NADH forms water and 3 ATP molecules in accordance with the following formula:

$$NADH+H^+ + \tfrac{1}{2}O_2 + 3\ Pi + 3\ ATP \rightarrow NAD^+ + 3\ ATP + 4H_2O.$$

Thus, with 1 NADH molecule, 3 ATP molecules are obtained which have an energy of approximately 21 kilocalories. This process is called oxidative phosphorylation. The supply of NADH and/or NADPH makes this work much easier for the organism, because it has greater energy reserves as a result.

More recently, NADH and NADPH and pharmaceutically acceptable salts thereof have been shown to be useful in the treatment of Parkinson's Disease. The effectiveness of these agents for this purpose is documented in my U.S. Pat. Nos. 4,970,200 and 5,019,561, the disclosures of which are incorporated herein by reference.

In addition, I have discovered that these substances are effective in the treatment of Morbus Alzheimer (i.e., Alzheimer's Disease), which is the subject of my U.S. Pat. No. 5,444,053.

Prior to my recent discoveries, NADH and NADPH have never been considered for therapeutic use, probably because it was believed that these compounds are rather unstable and, hence, not capable of being absorbed by the intestines of the human body. It would have been expected that these substances would be hydrolized in the plasma within a few seconds.

However, studies performed recently using NADH and NADPH demonstrate that these assumptions are incorrect. When NADH and NADPH were applied intravenously to patients with Parkinson's disease, a remarkable beneficial effect was observed which lasted at least 24 hours. See U.S. Pat. Nos. 4,970,200 and 5,019,561. This indicates that NADH and NADPH are not rapidly degraded in the plasma and blood.

SUMMARY OF THE INVENTION

It is an object of the invention to provide a new drug and method which is effective in the treatment of Chronic Fatigue Syndrome.

It is another object of the invention to provide a drug and method which is effective in alleviating symptoms of Chronic Fatigue Syndrome.

In accordance with the invention, the reduced form of nicotinamide adenine dinucleotide (NADH) or nicotinamide adenine dinucleotide phosphate (NADPH) or physiologically acceptable salts or derivatives of NADH and NADPH are administered to patients suffering from Chronic Fatigue Syndrome or the symptoms thereof. Daily single doses between 1 and 20 mg of NADH or NADPH, or mixtures thereof, may be used for effective treatment. Preferred doses are from 5 to 15 mg in the case of NADH and from 1 to 5 mg in the case of NADPH. It has been discovered that the administration of this endogenous substance as a pharmaceutical for the treatment of Chronic Fatigue Syndrome leads to surprising therapeutic results without any adverse side-effects. In patients suffering from Chronic Fatigue Syndrome, a clear alleviation of their symptoms, including but not limited to fatigue, headaches, depression and muscle pain and weakness, is achieved.

DETAILED DESCRIPTION OF THE INVENTION

When NADH, NADPH, or their physiologically tolerable salts are employed in accordance with the invention, they can be manufactured in the usual way with pharmaceutically acceptable fillers, or they can be incorporated for use as drugs into conventional galenic formulations for oral, parenteral, rectal, sublingual and nasal applications. The preparations can exist: in a solid form as tablets, capsules or coated tablets; in liquid form as a solution, suspension, spray or emulsions; in the form of suppositories, as well as in formulations having a delayed release of the active substances.

Suitable oral forms of NADH and NADPH which can be used in the practice of this invention are described in my U.S. Pat. No. 5,332,727, the disclosure of which is incorporated herein by reference. Both NADH and NADPH are very unstable at pHs below 7 which prevail within the confines of the stomach. Therefore, when used in oral form, these substances must be coated with an acid stable protective film so that they can survive the stomach environment for subsequent absorption by the intestine. Suitable acid stable coatings are known in the art and can be applied by a conventional coating process after the active ingredients are formed into a tablet or capsule. Examples of suitable coatings are: cellulose acetate phthalate; polyvinylacetate phthalate; hydroxyl-propyl-methyl cellulose phthalate; methacryllic acid copolymers; fat-wax; shellac; zein; aquacoating; and surerelease. Another possibility for the coating is a solution of a phthalate and a lack dry substance in isopropanol. An example of a suitable lack dry substance is sold under the name EUDRAGIT™ by Rohm Pharma. Alternatively, a protein coating in an aqueous medium may be applied. However, a sugar-caoting should not be used because it will destabilize NADH.

Although NADH and/or NADPH may be used by themselves in pure form (they are quite stable in compressed form when protected from light), it is preferred that they be combined in a galenic formulation with a stabilizer which is effective to inhibit oxidation of NADH and NADPH to the inactive oxidized forms $NAD^+$ and $NADP^+$, respectively. Most preferably, the NADH and/or NADPH is combined with both a stabilizer and a filler. It has been found that the following stabilizers are effective in inhibiting oxidation to the inactive $NAD^+$ and $NADP^+$ and result in the greatest shelf stability for NADH and NADPH: $NaHCO_3$; ascorbic acid and sodium ascorbate; tocopherols and tocopherolacetates; polyvinylpyrolidone ("PVP") 12 (12 representing the molecular weight 12,000); PVP 25; PVP 40; PVP PF 17 (meaning polymer having a molecular weight from 17,000) and PVP PF 60. NADH/NADPH formulations containing such stabilizers are stable for up to two years. Other various stabilizers will become apparent to those skilled in the art.

Suitable fillers for use with NADH and NADPH include: mannitol, microcrystalline cellulose, carboxymethyl cellulose; and dibasic calcium phosphate. Other suitable fillers will become apparent to those skilled in the art. Lactose should be avoided as a filler because it reacts with NADH.

In general, a preferred formulation will include about 3 to 10% by weight NADH and/or NADPH; about 1 to 10% by weight stabilizer; and a balance of filler. Such a formulation, after being compressed into a pill or tablet and coated, is stable for over 24 months.

The NADH and/or NADPH, together with the optional stabilizer and filler, may be formed into tablets, capsules, microtablets or micropellets by processes known in the art of pill manufacturing. Tablets may be formed either by direct compression or by granulation followed by compression. Capsules may be formed by blending the components and subsequently filling capsules with the blend using conventional automatic filling equipment. Microtablets may be formed by compressing powdered or granulated components into, e.g., 2 mm diameter tablets.

In the case of direct compression into tablets, a particularly preferred formulation is: NADH 5%, sodium ascorbate 5%, magnesium stearate 3%, talc 4%, silicon dioxide 1%, and mannitol 82%.

In the case of capsules, a particularly preferred formulation is: NADH 5%, sodium ascorbate 5%, polyvinylpyrolidone (PVP) 5%, microcrystalline cellulose 77%, magnesium stearate 3%, alpha-tocopherolacetate 1%, talc 3%, and silicon dioxide 1%.

Suitable physiologically acceptable salts of the coenzymes NADH and NADPH include all known physiologically acceptable acidic and basic salt-forming substances, for example: inorganic acids such as, for example, hydrochloric acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

For nasal administration, the NADH and/or NADPH may be taken in the form of a liquid spray or a powder spray, a gel, an ointment, an infusion, an injection or nose drops. Examples of liquid spray formulations are:

| NADH Liquid Spray Formulation | NADPH Liquid Spray Formulation |
|---|---|
| NADH 12 mg and Sodium ascorbate 36 mg, dissolved in 1 ml deionized water | NADPH 2.5 mg and Sodium ascorbate 36 mg, dissolved in 1 ml deionized water |
| 1 Spray dose is 0.13 ml containing 1.5 mg NADH | 1 Spray dose is 0.13 ml containing 0.32 mg NADPH |

For a powder spray, the NADH is simply ground into a fine powder and atomized from a spray bottle. Preferably, pure NADH is used for the powder spray, however, it can be used in conjunction with a filler, such as mannitol, as described below. The NADH which is inhaled through the nasal passages is absorbed by the mucosa of the nose and travels to the brain through the olfactory neural pathway. NADH administered in this manner has the same therapeutic effects as the oral form described above.

Thus, in accordance with the invention, the NADH may be administered to the nasal cavity of a patient afflicted with Chronic Fatigue Syndrome or symptoms thereof. The NADH (and/or NADPH) may be applied alone or in combination with other substances, for example, a pharmaceutically acceptable carrier or an agent that facilitates the transfer of the NADH through the nasal mucosa. The NADH is administered intranasally as a powder, spray, gel, ointment, infusion, injection or nose drops. The NADH is delivered to the nasal cavity. It is preferred that the NADH be delivered to the olfactory area in the upper third of the nasal cavity, and particularly to the olfactory neuroepithelium in order to promote transport of the NADH into the peripheral olfactory neurons rather than the capillaries within the respiratory epithelium. It is preferred that the transport of NADH to the brain be by means of the nervous system rather than the circulatory system so that the blood-brain barrier from the bloodstream into the brain is circumvented. However, good results can also be obtained through the bloodstream.

Surprisingly, it has been discovered that NADH (and NADPH) is capable of at least partially dissolving in the fluids that are secreted by the mucous membrane which surrounds the cilia of the olfactory receptor cells of the olfactory epithelium so that it may be absorbed into the olfactory neurons. The NADH may be combined with a carrier or other substance that fosters dissolution within nasal secretions, such as the ganglioside GM-1 or the phospolipid phosphatidylserine, or emulsifiers such as polysorbate 80. The NADH may be combined with micelles comprised of lipophilic substances which modify the permeability of the nasal membrane to enhance absorption of the NADH. Lipophilic micelles which are effective for this purpose include the gangliosides, the phospholipids and phosphatidylserine. Alternatively, the NADH may be combined with liposomes to enhance absorption of the NADH into the olfactory system.

I have also discovered that NADH (and/or NADPH) is effective in treating CFS and alleviating the symptoms thereof when administered sublingually. Like nasal administration, sublingual resorption of NADH achieves very fast results. The NADH is merely placed underneath the tongue and resorbed. Unlike the oral form of NADH described above, a sublingual form should not be coated with an acid stable protective coating.

It has also been discovered that good results are obtained when NADH (and/or NADPH) is administered rectally. However, results are not obtained as quickly as in the case of nasal or sublingual administration. NADH may be administered rectally in the form of suppositories. A suitable suppository formulations are:

| NADH Suppository Formulation | NADPH Suppository Formulation |
|---|---|
| NADH 5 mg | NADPH 2 mg |
| Sodium ascorbate 20 mg | Sodium ascorbate 20 mg |
| Suppository mass 2475 mg | Suppository mass 2478 mg |
| (Massa Novata BC, Henkel Inc) | (Maasa Novata BC, Henkel Inc) |

For all forms of administration (oral, sublingual, rectal, intravenous and nasal), the NADH or NADPH, or both, may be administered alone. The NADH and/or NADPH can also be used in combination with other active ingredients such as Coenzyme Q10, L-carnitine or L-glutathion.

METHOD OF ACTION

Without intending to be bound by any theory, it is believed that the mechanism of action in treating patients with Chronic Fatigue Syndrome may be two-fold in nature and centers about the ability of NADH (and/or NADPH) to: (1) stimulate cellular ATP production, and (2) stimulate endogenous L-dopa biosynthesis. Each of these possibilities will now be discussed.

(1) Stimulation of Cellular ATP Production

Since cellular ATP production is coupled to the NADH content in the cell, I believe that a medication which would help CFS patients regain their normal cellular energy production capacity is highly desirable. The more NADH present in a cell, the more ATP is produced, and the more energy a cell has available.

Current clinical literature reports of CFS patients support my proposed metabolic mechanism of action for CFS. CFS patients demonstrate: (a) low oxygen consumption, (b) early transition to anaerobic metabolism, and (c) disordered carnitine metabolism. This information is consistent with my belief that Chronic Fatigue Syndrome may be a metabolic/bioenergetics disorder.

In addition, evidence of liver dysfunction has been observed in most CFS cases. I believe that liver dysfunction, as well as central nervous system mitochondrial dysfunction, could explain the subacute encephalopathy so common in CFS patients.

Cognitive-evoked computer EEG brain maps of severely ill CFS patients are entirely consistent with a metabolic encephalopathy, including that seen in hepatic encephalopathy.

It is known that reduction in cellular ATP generation: (a) profoundly and adversely affects cellularly active transport systems, and (b) restricts the performance and capacity of organs and tissue which require high ATP concentrations. Organs adversely affected include the heart, brain and liver. Muscle tissues are also adversely affected.

To address the possible role of genetic damage in my metabolic/bioenergetics rationale for the treatment of CFS, I identified research directed at elucidating the role of somatic MtDNA mutations in neurodegeneration and its relation to this topic of mitochondrial energy production. An Emory University Medical School team using serial dilution-polymerase chain reaction methodology to analyze brain tissue specimens from individuals who died of Alzheimer's Disease/AD or Huntington's Disease found elevated levels of genetic mutations. The result showed a five-to eleven-fold greater deletion of the common mitochondrial 4977 nucleotide pair, mtDNA$^{4977}$, versus age-mathced controls.

(2) Stimulation of Endogenous L-Dopa Biosynthesis

Alternatively, or possibly in conjunction with the metabolic/bioenergetics enhancement proposal suggested above, NADH might act by stimulating the endogenous L-dopa biosynthesis. This has been demonstrated with pheochromocytoma cells. The dopamine production in these cells can be increased in a dosage dependent manner up to tenfold after administration of NADH. Furthermore, NADH stimulates tyrosine hydroxylase/TH activity in pheochromocytoma cells in a dosage dependent manner up to 70%.

These facts support the proposition that CFS may be a disease state of a metabolic/bioenergetics nature. Since cellular ATP production is coupled to the NADH content in the cell, a medication which would help CFS patients regain their normal cellular energy production capacity is highly unexpected. Furthermore, if NADH is found to increase endogenous L-dopa synthesis, then selected clinical manifestations of Chronic Fatigue Syndrome may also disappear.

From a classical bioenergetics perspective NADH serves as natural energy producer in the cells. The highest concentration of NADH is found in cells with the highest energy demands such as cardiac muscle and brain. NADH is a water-soluble, small molecule that transports electrons from the site where food molecules are metabolized, to the first of a series of electron carriers located in the mitochondria, the energy producing compartment of every cell. Almost all of the energy available from burning carbohydrates, fats, and other food is saved in the earliest stages of oxidation in the form of high energy electrons. These electrons, carried by NADH, are then combined with molecular oxygen within the respiratory chain. Because of the large amount of energy released by this reaction, NADH binds to enzymes in the inner membrane of the mitochondria to drive the conversion of ADP+$P_1$ to ATP.

NADH is a co-factor for a variety of enzymes. The majority of these enzymes catalyze oxidation-reduction/REDOX reactions. NADH is also involved in a number of normal cellular functions such as the ADP ribosylation of proteins, and the formation of cyclic ADP ribose. The most important function of NADH is in cell respiration. NADH uses oxygen to form water and ATP according to the following equation:

$$NADH+H^++\tfrac{1}{2}O_2+P_1+3ADP \to 3ATP+4H_2O+NAD^+$$

In this oxidative phosphorylation reaction, 1 mole of NADH produces 3 moles of ATP and about 21 kilocalories of energy.

As discussed above in my metabolic/bioenergetics perspective on Chronic Fatigue Syndrome, the decline in ATP production could be due to the inability of fixed postmitotic cells to regenerate their mitochondria. This would lead to a loss in the bioenergetic capacity of cells with concomitant decreases in ATP dependent protein synthesis and specialized physiological function. This would pave the way for degenerative diseases.

NADH ubiquinone reductase/Complex I dysfunction has been observed in a high percentage of patients with mitochondrial myopathy. The function and assembly of this enzyme is particularly susceptible to abnormalities of mitochondrial DNA involving either point mutation of the t-RNA genes or major deletions.

Specific preferred embodiments of the invention will now be described with reference to the following examples which should be regarded in an illustrative rather than a restrictive sense.

EXAMPLE I

A 42 year old female patient showed the following symptoms: fatigue for at least 6 months, mild fevers, sore throat, painful lymph nodes in the neck, muscle weakness, muscle pain, fatigue for 24 hours after exercising, headaches, joint pain and inability to concentrate. The patient's functional and cognitive performance was examined by a questionnaire yielding a score of 155 (a score of 200 is the worst case of Chronic Fatigue Syndrome, a score of 50 is normal for a healthy individual). The patient was diagnosed as suffering from Chronic Fatigue Syndrome. The patient was treated by administering 5 mg of NADH tablets daily for one month. After the treatment, upon examination of the patient, it was determined that her physical and cognitive performance had noticeably improved. Her score went down from 155 to 80 indicating that most of her complaints and symptoms had disappeared after NADH treatment, and only some of them occured some of the time. The NADH treatment was subsequently continued and the patient's condition improved somewhat further. The patients noticed a considerable improvement in physical and mental activites, in particular long term and short time memory. No Side effects were observed nor did the patient complain of any.

EXAMPLE II

A 55 year old female patient showed symptoms of fatigue for at least 6 months, sore throat, painful lymph nodes, muscle weakness, muscle pains, headache, short term memory problems, forgetfulness and inability to concentrate. The patient's score on the Chronic Fatigue questionnaire was 140, and consequently she was diagnosed as suffering from Chronic Fatigue Syndrome. The patient was treated by administering 5 mg of NADH tablets daily for one month. After the treatment, a physical examination revealed that the patient's symptoms were alleviated and her CFS score fell from 140 to 92. The patient reported an improvement in the energy level as reflected by increased exercise programs and shorter lasting fatigue after exercising. After the one month treatment period, NADH was discontinued for 8 weeks. The patient relapsed and exhibited symptoms very similar to the complaints reported before starting with NADH therapy. Her CFS score rose to 132. The patient was treated again by administering 5 mg of NADH tablets daily for one month. After the second treatment period the physical and mental performance improved considerably as revealed by the CFS score. Thereafter, the same four week long therapy was repeated every second month. The improvement of the patient's condition was maintained and no side effects were observed nor did the patient complain of any. The patient stated that she felt much better physically, as well as mentally, during the therapy.

EXAMPLE III

A female patient, 55 years of age, exhibited extreme fatigue for at least 6 months, mild fevers, sore throat, swollen neck glands, muscle weakness, headaches and inability to concentrate. The patient's CFS score was 158, leading to a diagnosis of Chronic Fatigue Syndrome.

The patient was administered 5 mg NADH daily orally for one month. An examination conducted after this treatment showed that the patient's CFS score went down to 96 and her symptoms had distinctly improved. Thereafter, the therapy with NADH was continued by administering 5 mg orally every day for more than 6 months. The patient's condition improved further to a CFS score of 76, and no side effects were observed during this extended therapy.

EXAMPLE IV

A 54 year old male patient was exhibiting distinct symptoms of Chronic Fatigue such as extreme fatigue for at least 6 months, sore throat, swollen neck glands, muscle weakness, muscle pain, headaches and some short term memory problems. The patient was diagnosed as suffering from Chronic Fatigue Syndrome. 2.5 mg of NADPH was administered intravenously three times a week for a period of 4 weeks. After the therapy, the patient exhibited distinct improvement in the CFS score. His score improved from 142 to 90. No side effects were observed during the treatment.

EXAMPLE V

A 48 year old female patient exhibited the major symptoms of Chronic Fatigue Syndrome, namely extreme fatigue which worsened with exercise and limited daily activity. She had swollen neck glands and unexplained muscle weakness, headaches as well as joint pain. Her CFS score was 162, and she also reported memory problems and forgetfulness.

2.5 mg of NADPH was administered intravenously three times a week for 4 weeks. An examination conducted after the therapy revealed that the patient's physical performance and capacity to exercise had significantly improved. The patient could perform physical exercise to a greater extent and with less problems afterwards. The symptoms of fatigueness occured only at very low frequency and they did not limit the patient's daily activity. Her CFS score dropped to 85 after the treatment period.

After the first treatment period the NADPH therapy was discontinued for 2 months and the patient's condition deteriorated to a CFS score of 128. After 3 months, the treatment with 2.5 mg of NADPH was restarted every other day for 4 weeks. During that treatment period the condition of the patient improved considerably. The CFS score fell again to 85. The patient stated that she felt much better physically as well as mentally during and after the second therapy.

In the foregoing specification the invention has been described with reference to specific exemplary embodiments thereof. It will, however, be evident that various modifications and changes may be made thereunto without departing from the broader spirit and scope of the invention as set forth in the appended claims. The specification should therefore be regarded in an illustrative rather than a restrictive sense.

What is claimed is:

1. A method of treating Chronic Fatigue Syndrome, comprising the step of administering to a patient suffering from Chronic Fatigue Syndrome an effective amount of NADH or NADPH, or a physiologically compatible salt of NADH or NADPH.

2. The method of claim 1 wherein the NADH or NADPH is administered intravenously.

3. The method of claim 1 wherein the NADH or NADPH is administered orally.

4. The method of claim 1 wherein the NADH or NADPH is administered sublingually.

5. The method of claim 1 wherein the NADH or NADPH is administered rectally.

6. The method of claim 1 wherein the NADH or NADPH is administered to a nasal passage of the human in need to result in absorption of the NADH or NADPH into the mucosa of the nose.

7. The method of claim 1 wherein the NADH or NADPH is administered in a dose of from 1 mg to 20 mg.

8. The method of claim 1 wherein NADH is administered in a dose of from 5 mg to 10 mg.

9. The method of claim 1 wherein NADPH is administered in a dose of from 1 mg to 5 mg.

10. The method of claim 8 wherein said dose is administered every 24 hours.

* * * * *

UNITED STATES PATENT AND TRADEMARK OFFICE
CERTIFICATE OF CORRECTION

PATENT NO. : 5,712,259
DATED : January 27, 1998
INVENTOR(S) : Joerg G.D. Birkmayer It is certified that error appears in the above-identified patent and that said Letters Patent is hereby corrected as shown below:

Column 8, lines 59-63, delete in its entirety and insert:

--1. A method for treating Chronic Fatigue Syndrome in a human, comprising administering to a human in need thereof, an amount of NADH or NADPH or a physiologically acceptable salt thereof, which is effective to abate said Chronic Fatigue Syndrome.--

Signed and Sealed this

Twenty-second Day of September, 1998

Attest:

BRUCE LEHMAN

*Attesting Officer*   *Commissioner of Patents and Trademarks*